(12) United States Patent
Ewaldsson et al.

(10) Patent No.: US 10,980,697 B2
(45) Date of Patent: Apr. 20, 2021

(54) METHOD OF ATTACHING AN ARTIFICIAL TENDON AND A PRODUCT

(71) Applicant: Bioservo Technologies Aktiebolag, Kista (SE)

(72) Inventors: Martin Oskar Gustaf Ewaldsson, Sigtuna (SE); Johan Ingvast, Åkersberga (SE)

(73) Assignee: BIOSERVO TECHNOLOGIES AKTIEBOLAG, Kista (SE)

( * ) Notice: Subject to any disclaimer, the term of this patent is extended or adjusted under 35 U.S.C. 154(b) by 768 days.

(21) Appl. No.: 15/569,348

(22) PCT Filed: Apr. 27, 2016

(86) PCT No.: PCT/EP2016/059409
§ 371 (c)(1),
(2) Date: Oct. 25, 2017

(87) PCT Pub. No.: WO2016/174091
PCT Pub. Date: Nov. 3, 2016

(65) Prior Publication Data
US 2018/0296421 A1    Oct. 18, 2018

(30) Foreign Application Priority Data
Apr. 29, 2015   (SE) .................... 1550532-4

(51) Int. Cl.
*A61H 1/02* (2006.01)
*A61F 5/01* (2006.01)

(52) U.S. Cl.
CPC .......... *A61H 1/0288* (2013.01); *A61F 5/0118* (2013.01); *A61H 1/0277* (2013.01);
(Continued)

(58) Field of Classification Search
CPC ................ A61H 1/0277; A61H 1/0288; A61H 2201/1638; A61H 2201/1645;
(Continued)

(56) References Cited

U.S. PATENT DOCUMENTS

| 5,631,861 A | 5/1997 | Kramer |
| 2010/0041521 A1* | 2/2010 | Ingvast .................. B25J 9/0006 482/49 |

(Continued)

FOREIGN PATENT DOCUMENTS

| CN | 101511310 A | 8/2009 |
| CN | 102811690 A | 12/2012 |

(Continued)

OTHER PUBLICATIONS

International Search Report from corresponding International Application No. PCT/EP2016/059409, dated Aug. 8, 2016.
(Continued)

*Primary Examiner* — Valerie L Woodward
(74) *Attorney, Agent, or Firm* — Tucker Ellis LLP

(57) ABSTRACT

Provided is a technique for attaching an artificial tendon to a support device having a supporting material as well as a product formed by the technique. The artificial tendon is provided for flexing or extending a joint of a body, when applied at the joint of the body, by way of pulling the artificial tendon along its lengthwise direction. The artificial tendon is attached to the support device by stitching across the tendon with a thread on the supporting material of the support device, which forms a tunnel for the artificial tendon between the supporting material and the stitching. The artificial tendon is able to travel in the tunnel. The tunnel formed by this technique is positioned on the surface of the supporting material of the support device.

12 Claims, 3 Drawing Sheets

(52) U.S. Cl.
CPC ............... *A61F 2005/0197* (2013.01); *A61F 2220/0075* (2013.01); *A61H 2201/165* (2013.01); *A61H 2201/1638* (2013.01); *A61H 2201/1645* (2013.01); *A61H 2201/1664* (2013.01)

(58) Field of Classification Search
CPC . A61H 2201/165; A61F 5/0118; A61F 5/013; A61F 5/01; A61F 2220/0075; A41D 19/015; B25J 9/00
See application file for complete search history.

(56) References Cited

U.S. PATENT DOCUMENTS

| | | | |
|---|---|---|---|
| 2012/0059290 A1* | 3/2012 | Yip | A61H 1/0288 601/40 |
| 2017/0049657 A1* | 2/2017 | Cortez | A61F 5/0118 |
| 2017/0168565 A1* | 6/2017 | Cohen | A61B 5/0022 |

FOREIGN PATENT DOCUMENTS

| | | |
|---|---|---|
| FR | 484487 A | 10/1917 |
| JP | 2001000462 A | 1/2001 |
| JP | 2005506736 A | 3/2005 |
| JP | 2010502266 A | 1/2010 |
| WO | 2004021936 A1 | 3/2004 |
| WO | 2008/027002 A1 | 3/2008 |

OTHER PUBLICATIONS

International Preliminary Report on Patentability from corresponding International Application No. PCT/EP2016/059409, dated Apr. 19, 2017.

* cited by examiner

METHOD OF ATTACHING AN ARTIFICIAL TENDON AND A PRODUCT

TECHNICAL FIELD

The present invention concerns a method of attaching an artificial tendon, a resulting product and a device having the resulting product.

BACKGROUND ART

Artificial tendons are used both for flexing and extending joints of human bodies, especially the joints of fingers. For example strengthening gloves are known, using different operating principles, using wires or cables, such as artificial tendons, in order to apply pushing and/or pulling forces onto particular points on each finger to be strengthened. For instance, electric or pneumatic driving mechanisms may be employed in order to pull the artificial tendons.

The artificial tendons are for example provided in sewn channels made of flexible material such as textile material, which are attached in support positions.

SUMMARY OF THE INVENTION

The present invention aims to provide a solution of attaching artificial tendons that is cost effective yet functional with a resulting product which is comfortable for the user.

According to a first aspect a method of attaching an artificial tendon at a support device having a supporting material is provided. The artificial tendon is provided for flexing or extending at least one joint of a body by means of pulling the artificial tendon along its lengthwise direction when it is applied at the joint of the body. The method comprises at least the step of stitching across the artificial tendon with a thread at the supporting material of the support device, which form a tunnel for the artificial tendon between the supporting material and the stitching, in which tunnel the artificial tendon may travel.

By means of the stitching across the artificial tendon the thread will be at least on both sides of the artificial tendon or even surrounding it and thus form a tunnel-like attachment to the supporting material.

This is an effective method of attaching an artificial tendon compared to sewing channels. Also, a flat appearance is provided, which is not affecting the comfort for the user. Another advantage is if low friction is provided between the thread and the artificial tendon so that the artificial tendon will easily slide against the thread. This can be accomplished if the thread or the artificial tendon has a low friction surface, for example made of a low friction material. Even better results will be achieved if both the artificial tendon and the thread has a low friction surface.

According to an embodiment of the method, it also comprises the step of providing a gap between neighbouring threads during stitching. Preferably the method also comprises the step stitching along a path of travel of the artificial tendon of the support device. During flexing, especially, of a joint material will crinkle up and become bulky but when threads are arranged with a gap they will instead just come closer or into contact but without bulging. Thus, it is a comfortable solution.

According to an embodiment of the method, the support device is an arm support or a supporting glove, such as a strengthening glove, for supporting flexing or extending of the joint with the artificial tendon.

According to another embodiment the method, the tunnel is provided on the inside of the supporting device. Preferably, the tunnel is covered with a thin textile material or mesh material on the stitch side, opposite the supporting material.

According to a second aspect of the present invention a tunnel for an artificial tendon to be able to travel in is provided. The tunnel is positioned at a surface of a supporting material of a supporting device and is formed by the supporting material and a stitching across the artificial tendon. Preferably, the stitching comprises a low friction thread. The stitching may also show a gap between neighbouring threads.

According to a third aspect of the present invention a strengthening glove having artificial tendons for flexing or extending at least one finger is provided. In the strengthening glove, the tendons run in a tunnel which is positioned at a surface of a supporting material of the strengthening glove and is formed by the supporting material and a stitching across the artificial tendon. Preferably, the stitching comprises a low friction thread.

According to an embodiment the strengthening glove is provided with a thin textile material or mesh material covering the tunnel as a lining inside the glove.

According to another embodiment of the strengthening glove, the artificial tendon runs between an actuator and a fixed point through the tunnel. Preferably the tunnel is provided along one side of a finger, over the top of the finger and along the other side of the finger.

SHORT DESCRIPTION OF DRAWINGS

Embodiments of the present invention will now be described in more detail under referral to the attached drawings, in which:

FIG. 1a-c shows a flexing support for at least one joint of a finger using an artificial tendon, where different stitching methods have been used.

DETAILED DESCRIPTION OF EMBODIMENTS

Figure 1A:
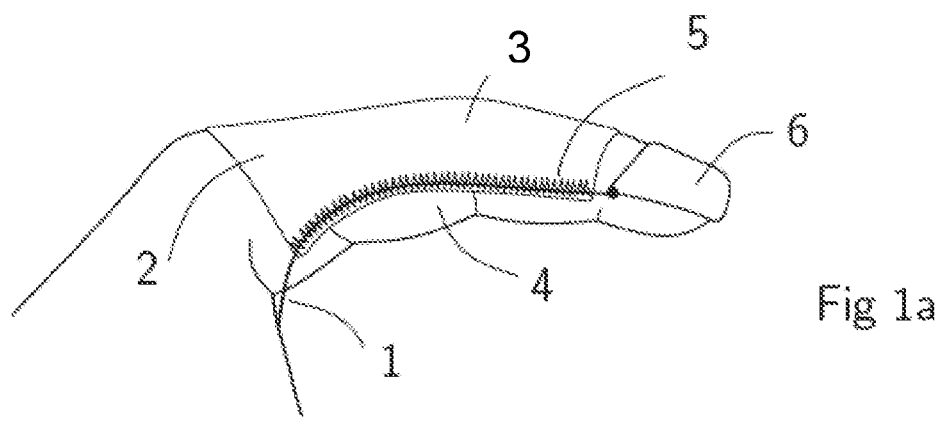

The present invention concerns a method of attaching an artificial tendon. In FIG. 1a an artificial tendon 1 is shown running along a supporting material 2. In use the support material 2, preferably being a part of a support device, is applied at, at least, one joint 3 of a body 4. This is preferably a human body although it is conceivable to be an animal, too.

The artificial tendon 1 is attached at the support material 2 by means of a stitching 5 crossing the tendon 1 in such a way as it is present at least on both sides of the artificial tendon 1. In the shown embodiment a zigzag stitching 5 has been performed across the artificial tendon 1 forming a tunnel 12 for the artificial tendon 1 to run in. The tunnel 12 is made up of the support material 2 and the stitching 5, see for example FIG. 4.

In the embodiment shown in FIG. 1a a fingertip cap 6 is arranged at the fingertip and is connected to the artificial tendon 1. The stitching 5 and thus tunnel 12 is made along the desired path of travel for the artificial tendon 1. The artificial tendon 1 may travel along one side of the finger up to the tip of the finger, to the cap 6 in the shown embodiment, and similarly on the opposite side of the finger. It is also conceivable that the artificial tendon 1 runs all the way around the tip of the finger, without any cap.

When a pulling force is applied to the artificial tendon 1 along its lengthwise direction it travels through the tunnel 12 and a flexing of the finger 4 is performed. The artificial tendon 1 is connected to an actuator (not shown), which applies the pulling force. Two artificial tendons 1 are provided in this embodiment, one on each side of the finger 4.

Figure 1B:
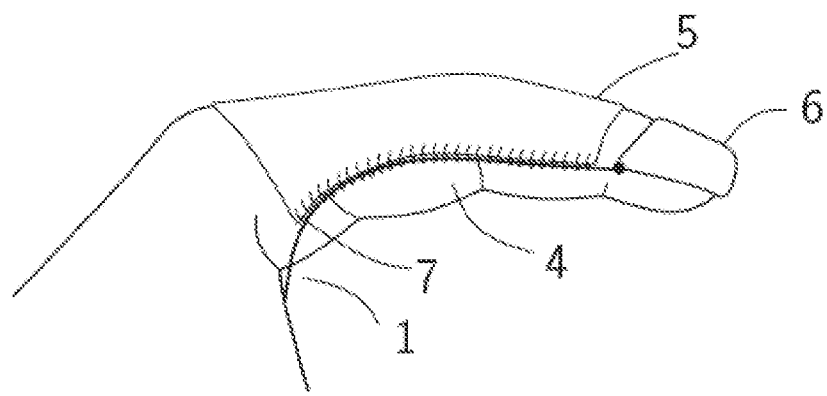
Figure 1C:
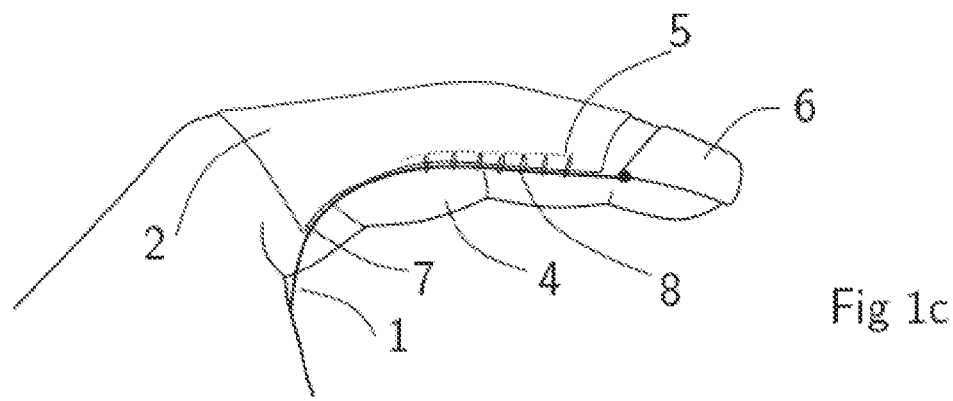

In FIG. 1b and 1c the artificial tendon 1 runs along an edge 7 of the support material 2. In FIG. 1b the thread goes from a first side of the support material 2 over the edge 7 and the artificial tendon 1 to the second, opposite side of the support material 2. Thus the artificial tendon 1 is more or less surrounded by the stitching 5.

In FIG. 1c the artificial tendon 1 is surrounded, more or less, at a distance of a stitch, at every stitch. This can be accomplished by using a straight stitching where the artificial tendon 1 is one of the two threads of the straight stitching. If the artificial tendon 1 is too tight and the other thread too loose, the thread will be forced up on the same side of the support material 2 as the artificial tendon 1 instead of meeting at the middle, inside of the material, forming a loop 8 around the artificial tendon 1. In such a way the artificial tendon 1 may run in tunnel 12 of loops 8 along the stitching.

If the threads in the stitching 5 is provided with a gap between neighbouring threads the stitching 5 will not become bulky when the artificial tendon 1 is pulled and the stitching will flex since the neighbouring threads will move towards and possibly against each other but do not have to bundle up.

Of course it is conceivable to use different kinds of stitching, such as overlock stitching, as long as the stitching 5 forms a tunnel 12.

Figure 2:
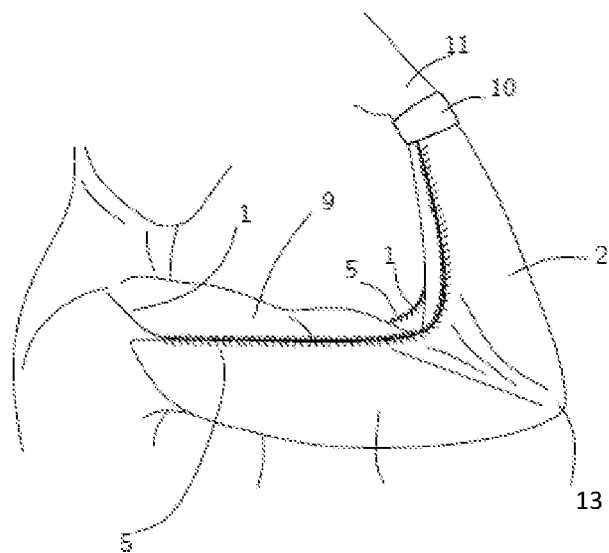
FIG. 2 shows a flexing support device for an arm.

The present invention may be used in a support device at a lot of different joints of a body, such as an arm, a shoulder, an ankle, a wrist, a knee. In FIG. 2 it is shown an embodiment of the invention, a support device for use at an arm joint 13. Also in this embodiment the artificial tendons 1 impart a flexing, of an arm 9 in this case. A support material 2 is provided along the outside of the arm 9 and the artificial tendons 1 are fixed in a collar 10 at the wrist 11. The stitching 5 may be of any type discussed above and form a tunnel for the artificial tendon 1 to travel in when pulled. Two artificial tendons 1 are provided, one on each side of the arm 9.

The support material 2 shown in FIG. 1-2 may suitably be arranged within a larger garment, if desired. For example a jacket or a glove. Most of the time the stitching, forming the tunnel, is provided on the inside of the garment. One reason is to protect the stitching and the artificial tendon from wear and another reason is not to interrupt the design of the garment.

When the stitching and artificial tendon is provided on the inside of the garment it is preferred to arrange a lining made of a mesh material or a thin textile material, thus enhancing comfort and minimizing the risk of catching the stitching with, for example, a nail.

Figure 3:
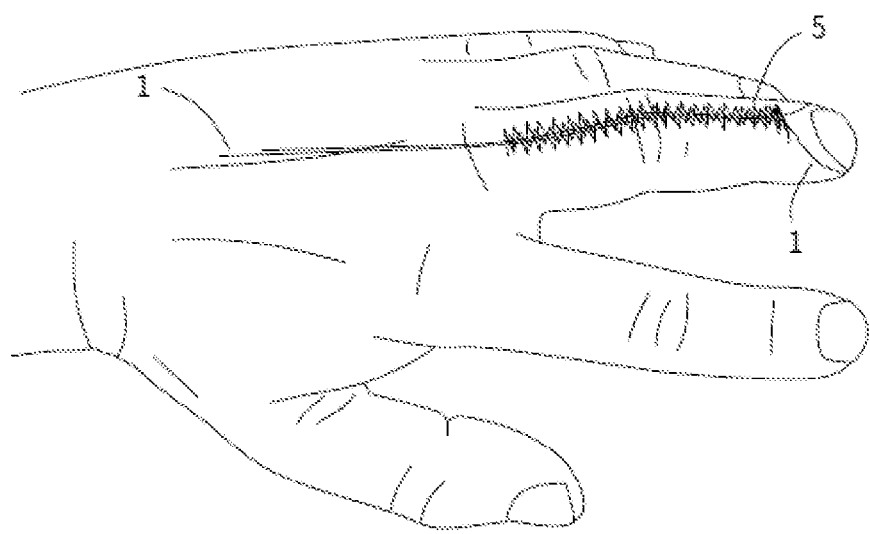
FIG. 3 shows an extending support device for a finger.

In FIG. 3 a case of extending a joint of a body is shown. The stitching 5 is of course arranged inside a glove or the like but for reason of clarity the glove is left out of the figure. The artificial tendon 1 runs in the tunnel formed by the stitching 5 and the glove (not shown) and when a pulling force is applied to the tendon 1 the finger will extend. The artificial tendon 1 runs along the dorsal side of the finger around the tip of the finger and back along the dorsal side of the finger, through the tunnel.

Figure 4:
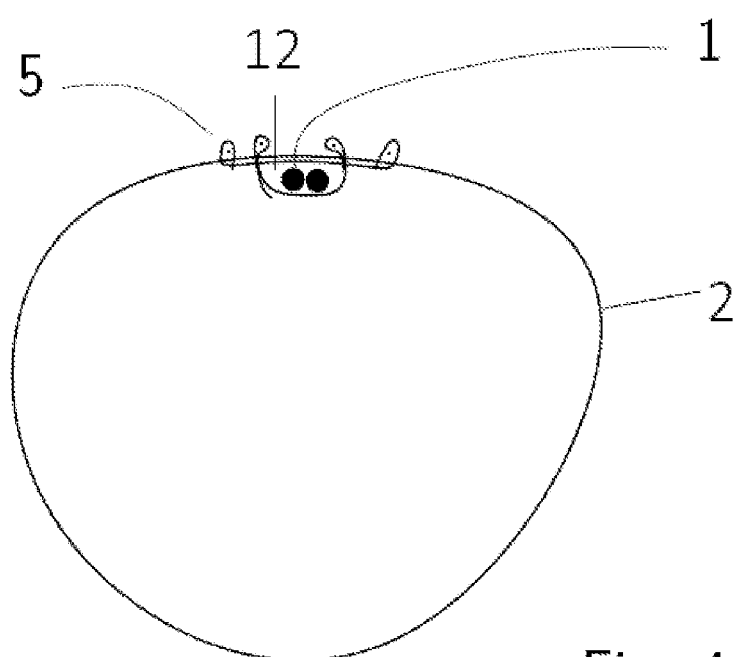
FIG. 4 shows a cross sectional view of an extending support for a finger.

In FIG. 4 a cross sectional view of a support material 2 or a glove finger and the stitching 5, which forms a tunnel 12 for the artificial tendons 1 to run through.

The invention is described by means of embodiments but can be altered in many ways within the scope of the appended claims.

The invention claimed is:

1. A method of attaching an artificial tendon to a support device having a supporting material, wherein the artificial tendon of the support device is provided for flexing or extending at least one joint of a body, when it is applied at the at least one joint of the body, by means of pulling the artificial tendon along its lengthwise direction, comprising:
   stitching across the artificial tendon with a thread on the supporting material of the support device, which forms a tunnel for the artificial tendon between the supporting material and the stitching, in which tunnel the artificial tendon is able to travel.

2. The method according to claim 1, further comprising: providing a gap between neighbouring threads during stitching.

3. The method according to claim 1, further comprising: stitching along a path of travel of the artificial tendon of the support device.

4. The method according to claim 1, whereby the tunnel is provided on the inside of the support device.

5. The method according to claim 1, further comprising: covering the tunnel with a thin textile material or mesh material on the stitch side, opposite the supporting material.

6. A tunnel for an artificial tendon to be able to travel in, positioned on a surface of a supporting material of a support device, wherein the artificial tendon of the support device is provided for flexing or extending at least one joint of a body, when it is applied at the at least one joint of the body, by means of pulling the artificial tendon along its lengthwise direction, wherein the tunnel comprises the supporting material and a stitching across the artificial tendon, thus making up the tunnel the artificial tendon is able to travel in.

7. The tunnel according to claim 6, wherein the stitching comprises a low friction thread.

8. The tunnel according to claim 6, wherein the stitching shows a gap between neighboring threads.

9. A strengthening glove having artificial tendons for flexing or extending at least one glove finger, in use, wherein the artificial tendons run in a tunnel according to claim 6.

10. The strengthening glove according to claim 9, wherein a thin textile material or mesh material is covering the tunnel as a lining inside the glove.

11. The strengthening glove according to claim 9, wherein the artificial tendon runs between an actuator and a fixed point, through the tunnel.

12. The strengthening glove according to claim 9, wherein the tunnel is provided along one side of the glove finger, over the top of the glove finger and along the other side of the glove finger.

\* \* \* \* \*